(12) United States Patent
Cheyene

(10) Patent No.: US 8,877,258 B1
(45) Date of Patent: Nov. 4, 2014

(54) HEALTH SUPPLEMENT USING GUARANA EXTRACT

(71) Applicant: Shaahin Cheyene, Venice, CA (US)

(72) Inventor: Shaahin Cheyene, Venice, CA (US)

( * ) Notice: Subject to any disclaimer, the term of this patent is extended or adjusted under 35 U.S.C. 154(b) by 20 days.

(21) Appl. No.: 13/751,151

(22) Filed: Apr. 17, 2013

(51) Int. Cl.

| | |
|---|---|
| *A01N 65/00* | (2009.01) |
| *A61K 36/41* | (2006.01) |
| *A61K 31/714* | (2006.01) |
| *A61K 31/4375* | (2006.01) |
| *A61K 36/53* | (2006.01) |
| *A61K 31/05* | (2006.01) |
| *A61K 31/685* | (2006.01) |
| *A61K 31/455* | (2006.01) |
| *A61K 31/198* | (2006.01) |
| *A61K 36/16* | (2006.01) |
| *A61K 36/534* | (2006.01) |
| *A61K 31/439* | (2006.01) |
| *A61K 31/522* | (2006.01) |
| *A61K 31/221* | (2006.01) |

(52) U.S. Cl.
CPC ............... *A61K 36/534* (2013.01); *A61K 36/41* (2013.01); *A61K 31/714* (2013.01); *A61K 31/4375* (2013.01); *A61K 36/53* (2013.01); *A61K 31/05* (2013.01); *A61K 31/685* (2013.01); *A61K 31/455* (2013.01); *A61K 31/198* (2013.01); *A61K 36/16* (2013.01); *A61K 31/439* (2013.01); *A61K 31/522* (2013.01); *A61K 31/221* (2013.01)
USPC .......................................................... 424/725

(58) Field of Classification Search
None
See application file for complete search history.

(56) References Cited

U.S. PATENT DOCUMENTS

2005/0181047 A1 * 8/2005 Romero ......................... 424/469

* cited by examiner

*Primary Examiner* — Michael Meller
(74) *Attorney, Agent, or Firm* — Jeffrey M. Furr, Esq.; Furr Law Firm

(57) ABSTRACT

The current invention is a supplement made from a combination of herbs, vitamins, amino acids which in the preferred embodiment is a 100% vegetarian liquid capsules that are ingested allow for rapid absorption. The components of the supplement can be mint or menthol such as peppermint or spearmint, Methyl B12 or B12, Niacin, Guarana, Dimethylaminoethanol, Acetyl-L-carnitine or ALCAR, Ocimum tenuiflorum, one or more teas such as green tea, white tea or black tea, Ginkgo, Rhodiola rosea, phosphatidylserine, Tyrosine, L-Alpha Glycerylphosphorylcholine, Citicoline (INN), Huperzine A, and Vinpocetine.

1 Claim, 1 Drawing Sheet

Components

Guarana mint or menthol such as peppermint or spearmint

Methyl B12

Niacin

Dimethylaminoethanol

Acetyl-L-carnitine or ALCAR

Ocimum tenuiflorum

One or more teas such as green, white or black tea

Ginkgo

Rhodiola rosea

Phosphatidylserine

Tyrosine

L-Alpha Glycerylphosphorylcholine

Citicoline (INN)

Huperzine A

Vinpocetine

HEALTH SUPPLEMENT USING GUARANA EXTRACT

CROSS-REFERENCES TO RELATED APPLICATIONS (IF ANY)

None.

BACKGROUND OF INVENTION

1. Field of the Invention

This device refers to the field of health supplements more practically one to improve brain function and activity.

2. Background

With the speed of today information highway improved brain function is vital. There are very few supplements that are designed specifically to assist in brain functioning and those that do not work very well.

There is still room for improvement in the art.

SUMMARY OF THE INVENTION

The current invention is a combination of herbs, vitamins, amino acids which in the preferred embodiment is a 100% vegetarian liquid capsules that are ingested allow for rapid absorption. The components of the supplement are as follows, mint or menthol such as peppermint or spearmint, Methyl B12 or B12, Niacin, Guarana, Dimethylaminoethanol, Acetyl-L-carnitine or ALCAR, Ocimum tenuiflorum, one or more teas such as green tea, white tea or black tea, Ginkgo, Rhodiola rosea, phosphatidylserine, Tyrosine, L-Alpha Glycerylphosphorylcholine, Citicoline (INN), Huperzine A, and Vinpocetine.

BRIEF DESCRIPTION OF THE DRAWINGS

FIG. 1 shows the components.

BRIEF DESCRIPTION OF THE PREFERRED EMBODIMENTS

There are a number of significant design features and improvements incorporated within the invention.

The current invention is a supplement that is a pioneering advancements in brain health. Clinical studies show that the ingredients found in the current invention improve memory, concentration, and alertness. Powered by superior ingredients such as citicoline and phosphatidylserine, the current invention is a non-prescription brain-health formula that can help support the brain and brain functioning. It is designed to be a brain health supplement designed to help support memory, focus, concentration and alertness.

The current invention is a combination of herbs, vitamins, amino acids which in the preferred embodiment is a 100% vegetarian liquid capsules that are ingested allow for rapid absorption.

As shown in FIG. 1, the components of the supplement are a combination of two or more of the following; mint or menthol such as peppermint or spearmint, Methyl B12 or B12, Niacin, Guarana, Dimethylaminoethanol, Acetyl-L-carnitine or ALCAR, Ocimum tenuiflorum, one or more teas such as green tea, white tea or black tea, Ginkgo, Rhodiola rosea, phosphatidylserine, Tyrosine, L-Alpha Glycerylphosphorylcholine, Citicoline (INN), Huperzine A, and Vinpocetine.

Along with the other functional ingredients, unique to the supplement is the use of Caffeine (naturally occurring) and mint or menthol. The key factors are that the mint opens up the breathing passageways and acts as a bronchial dialator while the caffeine brings about an immediate sense of alertness and well being. In the meanwhile the other functional brain health ingredients take effect.

The current invention's of the use of Methyl B12 as opposed to B12 will make the supplement more absorbable by a large percentage of the population who cannot absorb B12 in their bodies. This is a big improvement over the prior art. This is the preferred embodiment over the use of Vitamin B 12. Vitamin B12, vitamin B12 or vitamin B-12, also called cobalamin can be used, is a water soluble vitamin with a keyrole in the normal functioning of the brain and nervous system, and for the formation of blood.

The supplement contains ingredients like Phosphatidylserine that may block the release of the neurodegenerative hormone Cortisol in the human body. By blocking Cortisol, these ingredients may show potential for preventing neurodegenerative aging.

Vitamin B12, vitamin B12 or vitamin B-12, also called cobalamin, is a water soluble vitamin with a keyrole in the normal functioning of the brain and nervous system, and for the formation of blood.

Niacin (also known as vitamin B3, nicotinic acid and vitamin PP) is an organic compound and one of the forty to eighty essential human nutrients.

Guarana (/ˌgwarə ˈnaː/, from the Portuguese [gwaɾɐ ˈna], *Paullinia cupana*, syn. *P. crysan, P. sorbilis*) is a climbing plant in the maple family, Sapindaceae, native to the Amazon basin and especially common in Brazil. Guarana features large leaves and clusters of flowers, and is best known for its fruit, which is about the size of a coffee bean. As a dietary supplement, guarana is an effective stimulant: it contains about twice the caffeine found in coffee beans (about 2-4.5% caffeine in guarana seeds compared to 1-2% for coffee beans).

Kola nut is a caffeine-containing nut of Cola acuminata and Cola sharp, trees of the cocoa family. It is native to tropical Africa and cultivated extensively in the American tropics.

Dimethylaminoethanol, also known as DMAE or dimethylethanolamine, is an organic compound. Short-term studies have shown an increase in vigilance and alertness with a positive influence on mood following administration of DMAE, vitamins, and minerals. Research for attention deficit hyperactivity disorder (ADHD) has been promising, though inconclusive.

Acetyl-L-carnitine or ALCAR, is an acetylated form of L-carnitine. It is adietary supplement and naturally occurs in plants. ALCAR has the ability to cross the blood-brain barrier and get to the brain blood circulation, where it acts as a powerful antioxidant, which helps in prevention of the brain cells' deterioration. Its supplementation has been shown to be neuro-protective in instances of cerebral ischemia in rats and may be useful in treating peripheral nerve injury. It may have some neuroprotective benefit in the treatment of Parkinson's disease, but further research is required. This plant has a number of uses in Ayurveda and Ayurvedic medicine. Studies in humans show that an extract of the plant has anti-anxiety effects.

It is listed as a nootropic, a drug that enhances cognitive ability. In India, this plant has also been used traditionally to consecrate newborn babies in the belief that it will open the gateway of intelligence. Laboratory studies on rats indicate that extracts of the plant improve memory capacity and motor learning ability. Recent studies suggest bacopa may improve intellectual activity.

Peppermint (Mentha×piperita, also known as *M. balsamea* Willd.) is a hybrid mint, a cross between the watermint (*Mentha aquatica*) and spearmint (*Mentha spicata*). According to the international journal of neuroscience, the aroma of peppermint has been found to enhance memory. Some studies suggested that it can be administered by instructors to their students before examinations, to aid recall.

Ocimum tenuiflorum (also tulsi, tulasī, or Holy Basil) is an aromatic plant which is widely known across South Asia as a medicinal plant and an herbal tea, commonly used in Ayurveda. Tulsi is considered to be an adaptogen, balancing different processes in the body, and helpful for adapting to stress. Tulsi is regarded in Ayurveda as a kind of "elixir of life" and believed to promote longevity.

Green tea is made solely with the leaves of *Camellia sinensis*. Over the last few decades green tea has been subjected to many scientific and medical studies to determine the extent of its long-purported health benefits, with some evidence suggesting that regular green tea drinkers have lower chances of heart disease and of developing certain types of cancer. Although green tea does not raise the metabolic rate enough to produce immediate weight loss, a green tea extract containing polyphenols and caffeine has been shown to induce thermogenesis and stimulate fat oxidation, boosting the metabolic rate 4% without increasing the heart rate.

Ginkgo is believed to have nootropic properties, and is mainly used as memory and concentration enhancer. However, studies differ about its efficacy. The largest and longest independent clinical trial to assess Ginkgo biloba's ability to prevent memory loss has found that the supplement alone does not prevent or delay dementia or Alzheimer's disease.

According to some studies, Ginkgo can significantly improve attention in healthy individuals. In one such study, the effect was almost immediate and reaches its peak in 2.5 hours after the intake. One study suggests that Ginkgo's effect on cognition may be attributable to its inhibitory effect on norepinephrine reuptake.

Rhodiola rosea may be effective for improving mood and alleviating depression. Pilot studies on human subjects showed that it improves physical and mental performance, and may reduce fatigue. Rhodiola rosea's effects are potentially mediated by changes in serotonin and dopamine levels due tomonoamine oxidase inhibition and its influence on opioid peptides such as beta-endorphin, although these specific neuro-chemical mechanisms have not been clearly documented with scientific studies. Rhodiola is included among a class of plant derivatives called adaptogens which differ from chemical stimulants, such as nicotine, and do not have the same physiological effects.

The benefits of phosphatidylserine (PS) in cognitive enhancement applications is currently under study. First pilot studies indicate that PS supplementation might be beneficial for children with attention-deficit hyperactivity disorder. The FDA has given "qualified health claim" status to phosphatidylserine, stating that "Consumption of phosphatidylserine may reduce the risk of dementia in the elderly" and "Consumption of phosphatidylserine may reduce the risk of cognitive dysfunction in the elderly".

Tyrosine is one of the 20 amino acids that are used by cells to synthesize proteins. Tyrosine is a precursor to neurotransmitters and increases plasma neurotransmitter levels (particularly dopamine and norepinephrine) Improvements in cognitive and physical performance seen in human trials.

White tea comes from the delicate buds and younger leaves of the Chinese *Camellia sinensis* plant. White tea shares many of the same chemical properties and health effects of tea.

Black tea is a variety of tea that is more oxidized than the oolong, green, and white varieties. All four varieties are made from leaves of *Camellia sinensis*. Black tea is generally stronger in flavor and contains more caffeine than the less oxidized teas.

L-Alpha Glycerylphosphorylcholine (Alpha GPC, choline alfoscerate) is a natural choline compound found in the brain and in milk. It is also a parasympathomimetic acetylcholine precursor which may have potential for the treatment of Alzheimer's disease and is used as anootropic dietary supplement to enhance memory and cognition.

Alpha GPC rapidly delivers choline to the brain across the blood-brain barrier and is a biosynthetic precursor of the acetylcholine neurotransmitter. Alpha GPC is derived from highly purified soy lecithin.

Citicoline (INN), also known as cytidine diphosphate-choline (CDP-Choline) & cytidine 5'-diphosphocholine is a psychostimulant/nootropic. It is an intermediate in the generation of phosphatidylcholine from choline.

Huperzine A is a naturally occurring sesquiterpene alkaloid compound found in the plant firmoss Huperzia serrata. In the US, Huperzine A is sold as a dietary supplement for memory support. The botanical has been used in China for centuries for the treatment of swelling, fever and blood disorders. Clinical trials in China have shown it to be effective in the treatment of Alzheimer's disease and enhancing memory in students.

Vinpocetine (brand names: Cavinton, Intelectol; chemical name: ethyl apovincaminate) is an extract from the periwinkle (plant) Vinca minor. Vinpocetine is widely marketed as a supplement for vasodilation and as a nootropic for the improvement of memory. In other words, Vinpocetine may help support brain functions such as concentration and memory by activating cerebral metabolism. Vinpocetine has been identified as a potent anti-inflammatory agent that might have a potential role in the treatment of Parkinson's disease and Alzheimer's disease.

As to a further discussion of the manner of usage and operation of the present invention, the same should be apparent from the above description. Accordingly, no further discussion relating to the manner of usage and operation will be provided.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur by those skilled in the art, it is not desired to limit the invention to the exact construction and operation shown and described, and accordingly, all suitable modifications and equivalents may be resorted to, falling within the scope of the invention.

I claim:

1. A liquid capsule for improving brain function and activity in a human consisting essentially of therapeutically effective amounts of peppermint extract, spearmint extract, Methyl B12, Niacin, Guarana extract, Dimethylaminoethanol, Acetyl-L-carnitine, Ocimum tenuiflorum extract, green tea extract, white tea extract, black tea extract, Ginkgo extract, Rhodiola rosea extract, phosphatidylserine, Tyrosine, L-Alpha Glycerylphosphorylcholine, Citicoline, Huperzine A, and Vinpocetine.

\* \* \* \* \*